US010687910B1

(12) United States Patent
Chang et al.

(10) Patent No.: US 10,687,910 B1
(45) Date of Patent: Jun. 23, 2020

(54) ORTHOPEDIC SURGERY ASSISTANT SYSTEM AND END EFFECTOR

(71) Applicant: METAL INDUSTRIES RESEARCH&DEVELOPMENT CENTRE, Kaohsiung (TW)

(72) Inventors: Chin-Yu Chang, Kaohsiung (TW); Bing-Feng Huang, Kaohsiung (TW); Chih-Lung Lin, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 20 days.

(21) Appl. No.: 16/223,543

(22) Filed: Dec. 18, 2018

(51) Int. Cl.
A61B 34/00 (2016.01)
A61B 34/30 (2016.01)
A61B 90/50 (2016.01)
A61B 90/00 (2016.01)
A61B 17/88 (2006.01)
A61B 34/10 (2016.01)
A61B 17/66 (2006.01)
A61B 17/62 (2006.01)

(52) U.S. Cl.
CPC .............. *A61B 34/70* (2016.02); *A61B 17/88* (2013.01); *A61B 34/10* (2016.02); *A61B 34/25* (2016.02); *A61B 34/30* (2016.02); *A61B 90/06* (2016.02); *A61B 90/50* (2016.02); *A61B 17/62* (2013.01); *A61B 17/66* (2013.01); *A61B 2034/305* (2016.02); *A61B 2090/064* (2016.02)

(58) Field of Classification Search
CPC .......... A61B 34/70; A61B 34/10; A61B 34/30
See application file for complete search history.

(56) References Cited

U.S. PATENT DOCUMENTS

| 2001/0013764 | A1* | 8/2001 | Blumenkranz | ........ B25J 9/1689 318/568.11 |
| 2001/0020140 | A1* | 9/2001 | Kramer | ................ A61B 5/1071 600/595 |
| 2001/0025183 | A1* | 9/2001 | Shahidi | .................. A61B 90/10 606/130 |
| 2003/0029463 | A1* | 2/2003 | Niemeyer | .............. B25J 9/1689 128/898 |
| 2004/0070822 | A1* | 4/2004 | Shioda | ..................... A61B 1/04 359/372 |
| 2014/0379038 | A1 | 12/2014 | Dogramadzi et al. | |
| 2019/0192148 | A1* | 6/2019 | Shelton, IV | ..... A61B 17/07207 |

* cited by examiner

*Primary Examiner* — Christian A Sevilla
(74) *Attorney, Agent, or Firm* — WPAT, PC

(57) ABSTRACT

An orthopedic surgery assistant system includes: a multi-axis mechanical arm module; at least one end effector, including: two linear actuating elements, two actuating element encoders, a central annular structure, a connector, and a power/torque sensing element; a guide and positioning module; and a surgery remote control module, so that a user pulls the multi-axis mechanical arm and the end effector according to a real-time three-dimensional model, so that the multi-axis mechanical arm performs translation and rotation motions in a plurality of axial directions on an applied end, and the end effector performs a rotation motion of two degrees of freedom on the applied end.

10 Claims, 4 Drawing Sheets

ORTHOPEDIC SURGERY ASSISTANT SYSTEM AND END EFFECTOR

BACKGROUND

Technical Field

The present disclosure relates to an end effector, and in particular, to an end effector of an orthopedic surgery assistant system.

Related Art

At present, in an orthopedic trauma reduction surgery, a minimally invasive method accounts for approximately 60% of the total and has become a mainstream method. In domestic surgeries, fractures near hips account for a largest proportion, followed by long bones of limbs and wrists. A cavum pelvis is the part that has the greatest potential to be assisted by a robot. The most main problems that doctors at a clinical surgery end face are: (1) C-Arm needs to be continuously photographed in a reduction process, causing a large amount of radiation exposure for a doctor and a patient; (2) surrounding tissues have a great antagonism force (an applying force of approximately >100 N is needed on average), and a doctor may easily get tired during a surgery, affecting surgery applying quality; and (3) an image of a cross section of a tissue cannot be learned from C-Arm, and axial alignment is not easy.

US Patent Publication No. US20140379038A1 discloses a fracture reduction system for anatomy, where first and second manipulators, and optionally, a third manipulator are attached to a fragment of a fracture, to perform reduction through a percutaneous attachment apparatus such as a Schanz screw. A processing system determines, according to one or more medial images of a fracture, to correctly re-position and align fracture segments and perform rotation and translation operations on the fracture segments. The processing system provides a motion reference signal (a position, a speed, an accelerated speed, and a force) and collaborative actuation of the manipulators to a controller. However, in the prior art, operation of degrees of freedom of rotation of the front end is achieved by using movement of six linear actuating elements. Because the number of included actuating elements is relatively large, consequently, both a volume and a weight are relatively great, and costs are also high.

Therefore, it is necessary to provide an orthopedic surgery assistant system and an end effector, to resolve the foregoing problems.

SUMMARY

An objective of the present disclosure is to provide an orthopedic surgery assistant system, whose end effector uses two actuators to cooperate with a central annular mechanism, to achieve objectives of two degrees of freedom of rotation of an applied end and a light weight.

To achieve the foregoing objective, the present disclosure discloses an orthopedic surgery assistant system, including: a multi-axis mechanical arm module, including at least one multi-axis mechanical arm and configured to provide translation and rotation actions in a plurality of axial directions; at least one end effector, disposed at a front end of the multi-axis mechanical arm and including: two linear actuating elements, each including a drive lever; two actuating element encoders, respectively connected to the two linear actuating elements and configured to sense a position of the two linear actuating elements, to provide information about the position of the end effector; a central annular structure, mechanically connected to the two drive levers of the two linear actuating elements and configured to convert two linear motions of the two drive levers into a rotation motion of two degrees of freedom; a connector, disposed at a front end of the central annular structure and configured to clamp a tool; and a power/torque sensing element, disposed in the connector and configured to sense interactive forward forces and torque values between an applied end of the tool and an ambient environment; a guide and positioning module, scanning the applied end to get an image and converting the image from a two-dimensional image into a three-dimensional image to generate a real-time three-dimensional model of the applied end; and a surgery remote control module, electrically connected to the guide and positioning module, the multi-axis mechanical arm, and the end effector, so that a user pulls the multi-axis mechanical arm and the end effector according to the real-time three-dimensional model, so that the multi-axis mechanical arm performs translation and rotation motions in a plurality of axial directions on the applied end, and the end effector performs a rotation motion of two degrees of freedom on the applied end.

In the orthopedic surgery assistant system of the present disclosure, architecture design and research and development are performed on the orthopedic clinical trauma reduction surgery, and advantages thereof are: (1) the end effector of the present disclosure uses two actuators to cooperate with the central annular mechanism, to achieve objectives of two degrees of freedom of rotation, that is, pitch and yaw, of the applied end and a light weight; and (2) in the present disclosure, forward forces and torque sensing elements of six degrees of freedom are integrated, to sense an acting force of the fractured bone on surrounding soft tissues in a reduction process in real time and establish a power sensing and warning mechanism, to achieve secure trauma reduction assist; (3) a bone nail (for example, an orthopedic Schanz screw or another instrument) may be installed on the connector of the end effector of the present disclosure, to be connected to the in-vivo fractured bone in an in-vitro minimally invasive manner, perform direct movement operations of various degrees of freedom, and assist a doctor by cooperating with the guide and positioning module during the surgery.

DETAILED DESCRIPTION

To make the foregoing objective, characteristics, and features of the present disclosure more obvious and easily understood, related embodiments of the present disclosure are described below in detail with reference to the accompanying drawings.

Figure 1:
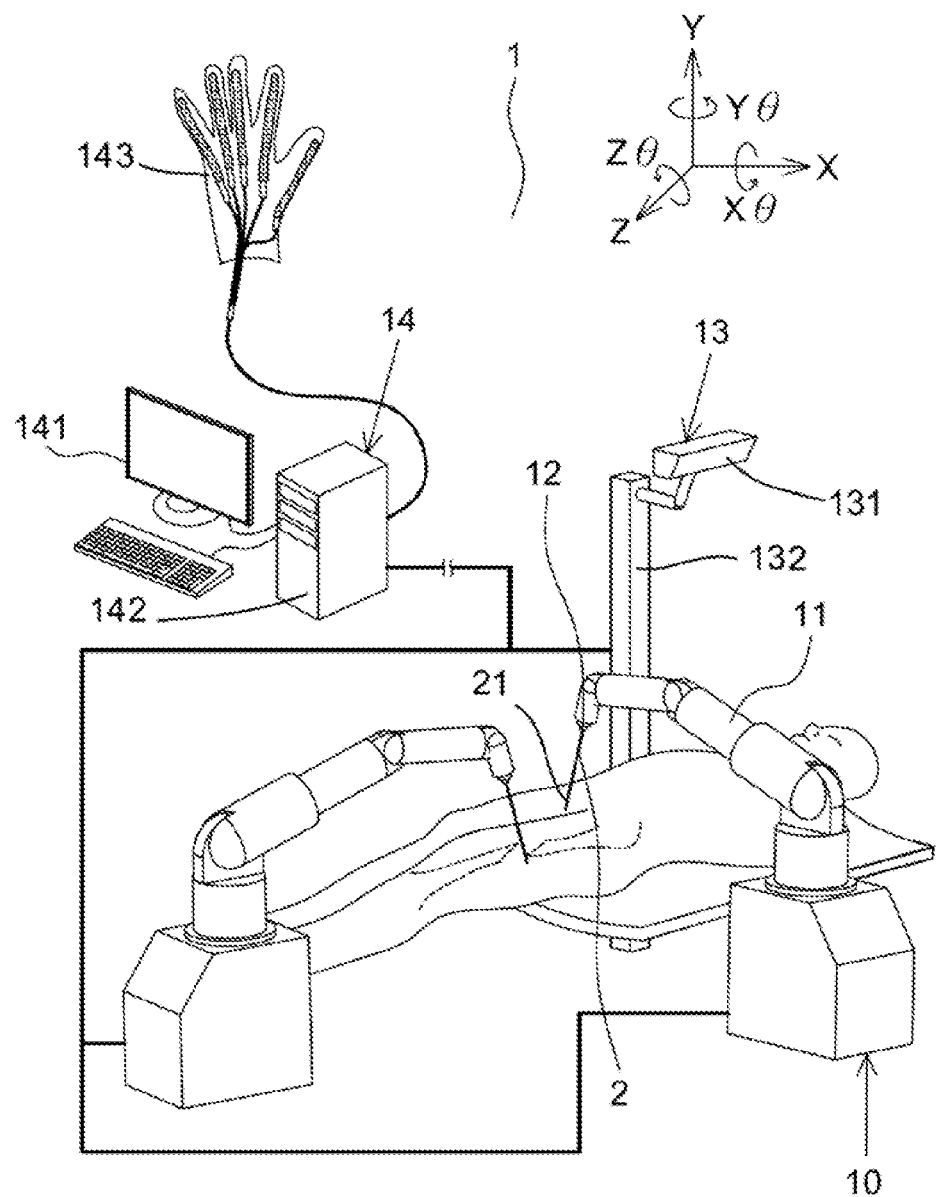
FIG. 1 is a schematic architectural diagram of an orthopedic surgery assistant system according to an embodiment of the present disclosure.
Figure 2:
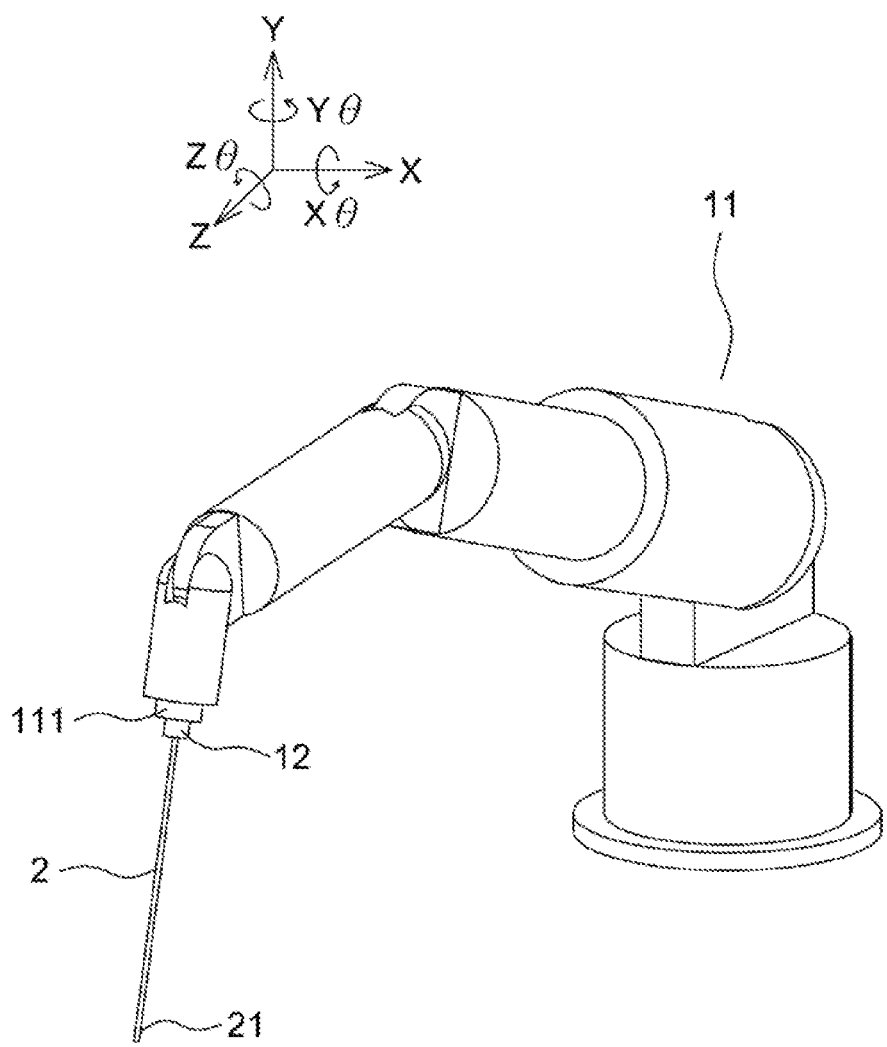
FIG. 2 is a schematic three-dimensional diagram of a multi-axis mechanical arm and an end effector according to an embodiment of the present disclosure.

FIG. 1 is a schematic architectural diagram of an orthopedic surgery assistant system according to an embodiment of the present disclosure. The orthopedic surgery assistant system may be applied to an orthopedic clinical trauma reduction surgery. Referring to FIG. 1 and FIG. 2, the orthopedic surgery assistant system 1 includes a multi-axis mechanical arm module 10, at least one end effector 12, a guide and positioning module 13, and a surgery remote control module 14. The multi-axis mechanical arm module 10 includes at least one multi-axis mechanical arm 11, configured to provide translation and rotation actions in a plurality of axial directions. The multi-axis mechanical arm 11 may be a six-axis mechanical arm, configured to provide translation X, Y, and X in three axial directions and rotation Xθ, Yθ, and Zθ in three axial directions. Six axial directions may also be regarded as six degrees of freedom. For example, the serially connected six-axis mechanical arm has variable impedance control, a doctor can pull the six-axis mechanical arm, and the six-axis mechanical arm provides stable power and auxiliary functions of maintaining and limiting positions during a surgery.

Figure 3:
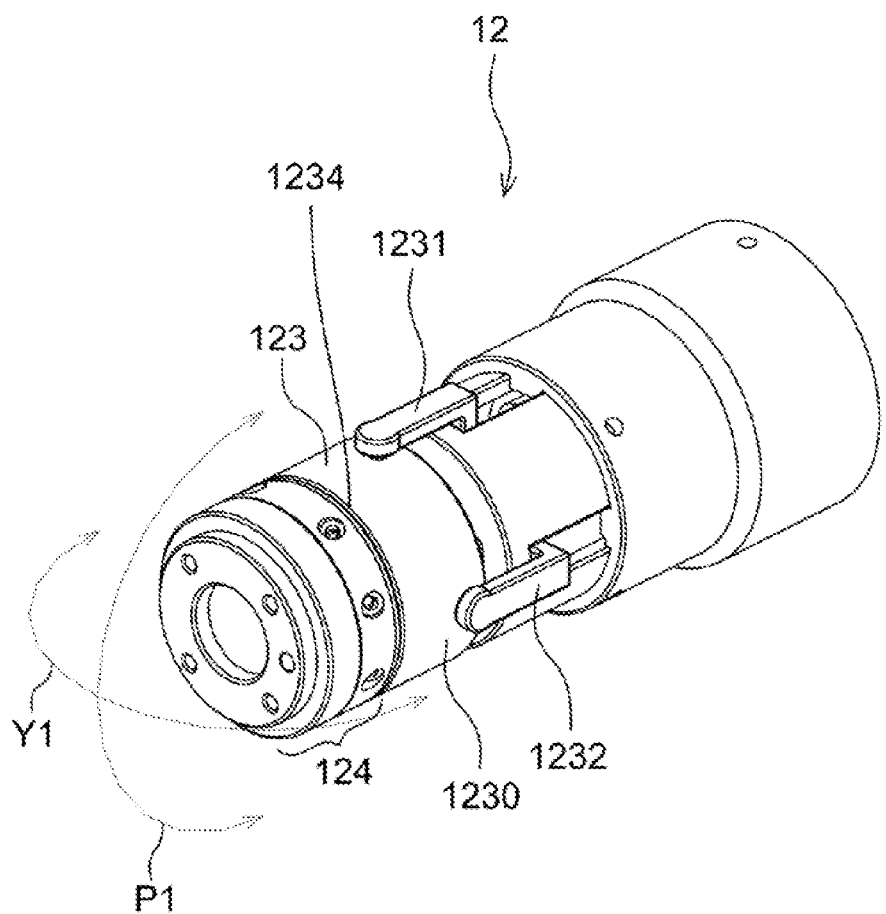
FIG. 3 is a schematic combined three-dimensional diagram of an end effector according to an embodiment of the present disclosure.
Figure 4:
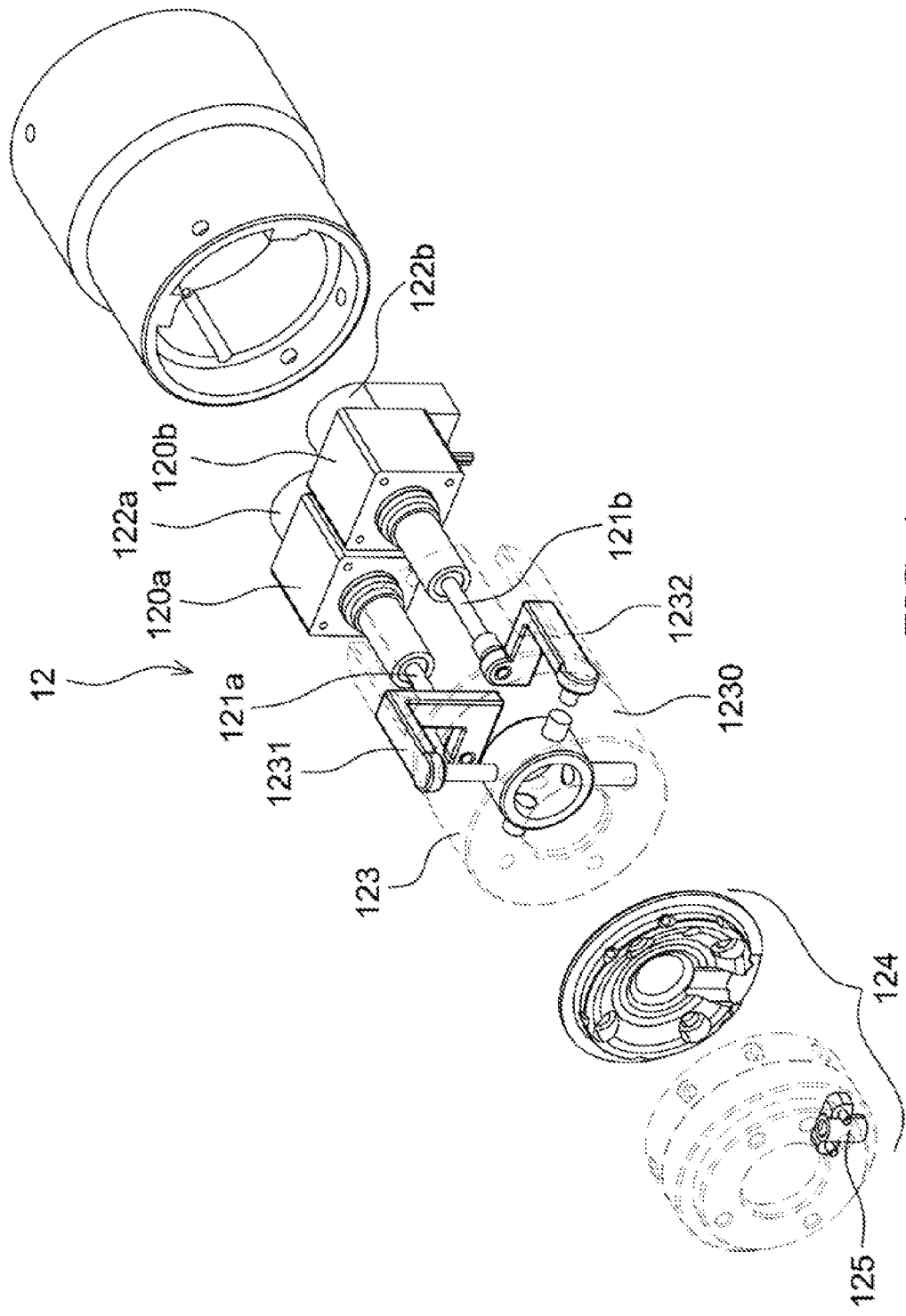
FIG. 4 is a schematic exploded three-dimensional diagram of an end effector according to an embodiment of the present disclosure.

Referring to FIG. 2, FIG. 3, and FIG. 4, the end effector 12 is disposed at a front end 111 of the multi-axis mechanical arm 11 and includes: two linear actuating elements 120a, 120b, two actuating element encoders 122a, 122b, a central annular structure 123, a connector 124, and a power/torque sensing element 125. The two linear actuating elements 120a, 120b each include a drive lever 121a, 121b. The two actuating element encoders 122a, 122b are respectively connected to rear ends of the two linear actuating elements 120a and 120b and configured to sense a position of the two linear actuating elements 120a, 120b, to provide information about the position of the end effector 12. The central annular structure 123 is mechanically connected to the two drive levers 121a, 121b of the two linear actuating elements 120a, 120b and configured to convert two linear motions of the two drive levers 121a, 121b into a rotation motion of two degrees of freedom. The rotation motion of two degrees of freedom is a pitch motion P1 and a yaw motion Y1.

In detail, the central annular structure 123 of the end effector 12 includes a central annular body 1230, a pitch link member 1231, and a yaw link member 1232. One end of the pitch link member 1231 and one end of the yaw link member 1232 are separately pivotedly connected to the central annular body 1230, and the other end of the pitch link member 1231 and the other end of the yaw link member 1232 are respectively connected to the two drive levers 121a, 121b of the two linear actuating elements 120a, 120b, so that the two drive levers 121a, 121b drive the central annular body 1230 to perform a pitch motion P1 and a yaw motion Y1. For example, when the drive lever 121a of the linear actuating element 120a drives only the pitch link member 1231, because the central annular body 1230 may be considered to be pivotedly connected to a left side and a right side, in this case, the central annular body 1230 produces the pitch motion P1. Similarly, when the drive lever 121b of the linear actuating element 120b drives only the yaw link member 1232, because the central annular body may be considered to be pivotedly connected to an upper side and a lower side, in this case, the central annular body 1230 produces the yaw motion Y1.

The connector 124 is disposed at a front end 1234 of the central annular structure 123 and configured to clamp a tool 2 (for example, a bone nail). For example, the connector 124 has a jaw gripping design and can clamp a bone nail.

The power/torque sensing element 125 is disposed in the connector 124 and configured to sense interactive forward forces and torque values between an applied end 21 of the tool 2 and an ambient environment. The power/torque sensing element 125 may be a six-axis power/torque sensor. For example, the power/torque sensing element 125 provides real-time display of interactive forward forces and torque sensing values (having six degrees of freedom in total) between a fractured bone and surrounding soft tissues, and provides accumulated data of quantized data reference and a subsequent surgery to a doctor.

Therefore, the end effector 12 may use two linear actuators 120a and 120b, to drive a pitch link member and a yaw link member of the central annular mechanism 123, to achieve objectives of two degrees of freedom of rotation of the applied end 21 and a light weight.

Referring to FIG. 1 again, the guide and positioning module 13 scans of the applied end 21 to get an image and converts the image from a two-dimensional (2D) image into a three-dimensional (3D) image to generate a real-time three-dimensional (3D) model of the applied end 21. In detail, the guide and positioning module 13 includes a scanning unit 131 and a software unit 132. The scanning unit 131 scans the applied end 21 to get the image, and the software unit 132 converts the image from a two-dimensional (2D) image into a three-dimensional (3D) image to generate the real-time three-dimensional (3D) model of the applied end 21. Therefore, the guide and positioning module 13 has a function of converting a medical image from a two-dimensional (2D) image into a three-dimensional (3D) image, provides generation of a real-time three-dimensional (3D) fractured bone model, displays a relative position of an in-vivo fractured bone, and provides relative position reference and visual feedback during reduction to a doctor.

The surgery remote control module 14 is electrically connected to the guide and positioning module 13, the multi-axis mechanical arm 11, and the end effector 12 in, for example, a bus cable manner or a wireless network manner, so that a user (for example, a doctor) pulls the multi-axis mechanical arm 11 and the end effector 12 according to the real-time three-dimensional (3D) model, so that the multi-axis mechanical arm 11 performs translation and rotation motions in a plurality of axial directions (for example, translation X, Y, and Z in three axial directions and rotation Xθ, Yθ, and Zθ in three axial directions) on the applied end 21, and the end effector 12 performs a rotation motion of two degrees of freedom (for example, a pitch motion and a yaw motion) on the applied end 21. For example, the surgery remote control module 14 includes a screen 141, and the relative position of the in-vivo fractured bone is displayed through the screen 141. The surgery remote control module 14 makes, by using a three-dimensional (3D) controller 142 or an intuitive gesture action controller 143, the multi-axis mechanical arm 11 perform manipulation of translation of three degrees of freedom and rotation of three degrees of freedom on the fractured bone, and the end effector 12 performs a rotation motion of two degrees of freedom on the fractured bone, to provide an accurate and effort-saving reduction function to a doctor.

According to the orthopedic clinical trauma reduction surgery of this embodiment, in step 1, a surgery applying person (for example, a doctor) applies an orthopedic bone nail (for example, a Schanz screw) to a fractured bone in the body of a patient in a minimally invasive manner before a surgery. In step 2, a positioning mark of the guide and positioning module is applied to an individual fractured bone, and then the scanning unit scans a medical image before the surgery, and the software unit converts a two-dimensional image into a three-dimensional image, to generate the three-dimensional (3D) stereoscopic image model of the fractured bone. In step 3, the six-axis mechanical arm and the end effector of the six-axis mechanical arm in a low impedance mode may be pulled to be connected to and fixed to the bone nail. In step 4, after the bone nail is fixed, a doctor may accurately perform reduction and fixing of the fractured bone through a controller and sensing feedback information in a mode of using the surgery remote control module for a remote-end surgery.

In the orthopedic surgery assistant system of the present disclosure, architecture design and research and development are performed on the orthopedic clinical trauma reduction surgery, and advantages thereof are: (1) the end effector of the present disclosure uses two actuators to cooperate with the central annular mechanism, to achieve objectives of two degrees of freedom of rotation, that is, pitch and yaw, of the applied end and a light weight; and (2) in the present disclosure, forward forces and torque sensing elements of six degrees of freedom are integrated, to sense an acting force of the fractured bone on surrounding soft tissues in a reduction process in real time and establish a power sensing and warning mechanism, to achieve secure trauma reduction assist; (3) a bone nail (for example, an orthopedic Schanz screw or another instrument) may be installed on the connector of the end effector of the present disclosure, to be connected to the in-vivo fractured bone in an in-vitro minimally invasive manner, perform direct movement operations of various degrees of freedom, and assist a doctor by cooperating with the guide and positioning module during the surgery.

In conclusion, only preferred implementations or embodiments of technical means, used to present and resolve the problems, of the present disclosure are described and are not intended to limit the scope of patent implementation of the present disclosure. Any equivalent change or modification that meets content of the claims of the present disclosure or that is made according to the claims of the present disclosure shall be covered by the claims of the present disclosure.

What is claimed is:

1. An orthopedic surgery assistant system, comprising:
a multi-axis mechanical arm module, comprising at least one multi-axis mechanical arm and configured to provide translation and rotation actions in a plurality of axial directions;
at least one end effector, disposed at a front end of the multi-axis mechanical arm and comprising:
two linear actuating elements, each comprising a drive lever;
two actuating element encoders, respectively connected to the two linear actuating elements and configured to sense a position of the two linear actuating elements, to provide information about the position of the end effector;
a central annular structure, mechanically connected to the two drive levers of the two linear actuating elements and configured to convert two linear motions of the two drive levers into a rotation motion of two degrees of freedom;
a connector, disposed at a front end of the central annular structure and configured to clamp a tool; and
a power/torque sensing element, disposed in the connector and configured to sense interactive forward forces and torque values between an applied end of the tool and an ambient environment;
a guide and positioning module, scanning the applied end to get an image and converting the image from a two-dimensional image into a three-dimensional image to generate a real-time three-dimensional model of the applied end; and
a surgery remote control module, electrically connected to the guide and positioning module, the multi-axis mechanical arm, and the end effector, so that a user pulls the multi-axis mechanical arm and the end effector according to the real-time three-dimensional model, so that the multi-axis mechanical arm performs translation and rotation motions in a plurality of axial directions on the applied end, and the end effector performs a rotation motion of two degrees of freedom on the applied end.

2. The orthopedic surgery assistant system according to claim 1, wherein the rotation motion of two degrees of freedom performed by the end effector on the applied end is a pitch motion and a yaw motion.

3. The orthopedic surgery assistant system according to claim 2, wherein the central annular structure of the end effector comprises a central annular body, a pitch link member, and a yaw link member, one end of the pitch link member and one end of the yaw link member are separately pivotedly connected to the central annular body, and the other end of the pitch link member and the other end of the yaw link member are respectively connected to the two drive levers of the two linear actuating elements, so that the two drive levers drive the central annular body to perform a pitch motion and a yaw motion.

4. The orthopedic surgery assistant system according to claim 2, wherein the power/torque sensing element is a six-axis power/torque sensor.

5. The orthopedic surgery assistant system according to claim 1, wherein the multi-axis mechanical arm is a six-axis mechanical arm, configured to provide translation in three axial directions and rotation in three axial directions.

6. The orthopedic surgery assistant system according to claim 2, wherein the guide and positioning module comprises a scanning unit and a software unit, the scanning unit scans to get the image the applied end, and the software unit converts the image from a two-dimensional image to a three-dimensional image to generate the real-time three-dimensional model of the applied end.

7. An end effector, comprising:
two linear actuating elements, each comprising a drive lever;
two actuating element encoders, respectively connected to the two linear actuating elements and configured to sense a position of the two linear actuating elements, to provide information about the position of the end effector;
a central annular structure, mechanically connected to the two drive levers of the two linear actuating elements and configured to convert two linear motions of the two drive levers into a rotation motion of two degrees of freedom;
a connector, disposed at a front end of the central annular structure and configured to clamp a tool; and
a power/torque sensing element, disposed in the connector and configured to sense interactive forward forces and torque values between an applied end of the tool and an ambient environment.

8. The end effector according to claim 7, wherein the rotation motion of two degrees of freedom performed by the end effector on the applied end is a pitch motion and a yaw motion.

9. The end effector according to claim 8, wherein the central annular structure of the end effector comprises a central annular body, a pitch link member, and a yaw link member, one end of the pitch link member and one end of the yaw link member are separately pivotedly connected to the central annular body, and the other end of the pitch link member and the other end of the yaw link member are respectively connected to the two drive levers of the two linear actuating elements, so that the two drive levers drive the central annular body to perform a pitch motion and a yaw motion.

10. The end effector according to claim 7, wherein the power/torque sensing element is a six-axis power/torque sensor.

* * * * *